| United States Patent [19] | [11] Patent Number: 4,517,793 |
| Carus et al. | [45] Date of Patent: May 21, 1985 |

[54] RADIO OPAQUE FIBRE

[75] Inventors: Edmund H. Carus, Darwen; Eric F. T. White, Alderley Edge, both of England

[73] Assignee: Vernon-Carus Limited, Darwen, England

[21] Appl. No.: 525,768

[22] Filed: Aug. 23, 1983

[51] Int. Cl.³ .......................... D02G 3/02; D02G 3/00
[52] U.S. Cl. ...................... 57/243; 428/372; 428/364; 428/373; 428/401; 524/140; 524/161; 523/204
[58] Field of Search .............. 428/364, 372, 373, 401; 524/140, 161, 423; 523/200, 204; 57/243, 244

[56] References Cited

U.S. PATENT DOCUMENTS

| 3,262,257 | 7/1966 | Martin | 428/364 |
| 4,221,697 | 9/1980 | Osborn et al. | 524/853 |
| 4,452,841 | 6/1984 | Oliveira | 524/423 |

*Primary Examiner*—George F. Lesmes
*Assistant Examiner*—Beverly K. Johnson
*Attorney, Agent, or Firm*—Fleit, Jacobson, Cohn & Price

[57] ABSTRACT

This invention provides a radio opaque fibre comprising polypropylene, a coupling agent and 55% to 70% of barium sulphate. The coupling agent is preferably isopropyl triisostearoyl titanate. The fibre finds particular application in manufacture of surgical swabs and dressings.

14 Claims, No Drawings

RADIO OPAQUE FIBRE

BACKGROUND OF THE INVENTION

This invention relates to fibres, yarns or threads which include radio opaque material.

Radio opaque multifilament yarns are included in surgical swabs so that they can be identified by X-rays. Such yarns must contain at least 55% by weight of radio opaque material in order to meet the specification of the British Pharmacopoeia. In the past, radio opaque yarns have been produced from viscose loaded with up to 60% barium sulphate. However these yarns possessed several shortcomings. The viscose component was affected by wet processing of the yarn during incorporation into woven gauze. Length changes occurred and excessive tensions were apparent. The viscose component was subject to brittle fracture at low stress leading to fragmentation. The nature of the wet spinning process made it very difficult to maintain product consistency.

Polypropylene has been assessed as an alternative carrying medium to viscose. Polypropylene being hydrophobic is not subject to dimensional changes caused by wet processing. Barium loaded polypropylene yarns have been made. However at loadings in excess of 45% by weight extensive loss of strength has been observed in multifilament yarns. Extrusion of filaments at loadings in excess of 45% has been difficult due to barium sulphate agglomeration. Twisting the low strength filaments also poses many difficulties.

SUMMARY OF THE INVENTION

We have now discovered that if a coupling agent is applied between the barium sulphate and the polypropylene as a monomolecular layer on the filler, yarns of higher intrinsic strength with enhanced spinnability can be obtained.

According to a first aspect of the present invention there is provided a radio opaque fibre comprising polypropylene a coupling agent and 55% to 70% by weight of barium sulphate.

There is preferably 60% to 70% of barium sulphate present, more preferably 65% to 70% of barium sulphate.

The coupling agent may be selected from the many which are used in relation to polypropylene. Titanium-containing coupling agents have been found to be particularly appropriate. Silanes may be used alternatively. Preferred silanes include vinyl triethoxysilane, vinyl tris(2-methoxyethoxy)silane, γ-methacryloxypropyltrimethoxysilane, β-(3,4-epoxycyclohexyl)ethyl trimethoxysilane, γ-glycidoxypropyl trimethoxysilane, γ-aminopropyl triethoxysilane and N-β-(aminoethyl)-γ-aminopropyl trimethoxysilane. The silanes disclosed in U.S. Pat. No. 3,715,371 may also be used. Chlorinated paraffins such as Chlorez 700 (Kenrich Petrochemicals Inc.) may also be used.

Preferred embodiments of the invention comprise one or more titanate coupling agents. Isopropyl trialkanoyl titanates are especially preferred. Isopropyl triisostearoyl titanate has been found to be particularly effective. Alternatively isopropyl tridodecylbenzenesulphonyl titanate may be employed. Phosphate or pyrophosphate derivatives may be used, including isopropyl tri(dioctylphosphate)titanate, isopropyl tri(dioctylpyrophosphate)titanate and titanium di(dioctylpyrophosphate)oxyacetate. Other titanate coupling agents manufactured by Kenrich Petrochemicals Inc., may be used.

Titanate coupling agents may be used in amounts of 0.5% by 5% by weight of barium sulphate, an amount of 0.4% to 1% being preferred.

The compounded polypropylene should preferably have a melt flow index not less than 12.

Multifilament fibre is preferred although monofilament fibre or tape may be employed.

The fibre may incorporate a dye, in accordance with medical practice. For example Cobalt Blue (Med) may be employed.

Multifilament fibre in accordance with the invention may have a twist factor of 4 to 5 turns per inch (1.6 to 2 turns per cm).

Multifilament fibre in accordance with the invention may have a thickness equivalent to 3300 to 3500 decitex (0.33 to 0.36 gm$^{-1}$).

According to a second aspect of the present invention a method of preparation of radio opaque fibre as hereinbefore disclosed comprises combining powdered barium sulphate with the coupling agent, mixing with the polypropylene and extruding the mixture.

The polypropylene is preferably powdered although chips may also be used.

The barium sulphate preferably has a particle size of not greater than 0.5μ.

The extrusion is preferably carried out under conditions normally used for extruding pure polypropylene with a melt flow index which is not less than 12. However the spinning temperature may be lowered to prevent formation of bubbles in the fibres. Preferred spinning temperatures lie in the range 190°–210° C.

Extrusion in a vertical direction is preferred to minimise breakage of the fibre. A drawdown length in excess of 1 m may be employed.

Spin finishing of the fibre is not essential but treatment with a smooth amount of liquid paraffin can be beneficial.

EXAMPLES

The following Examples further illustrates the invention.

EXAMPLE 1

Barium sulphate (60 parts, w/w, particle size of 0.5μ) was weighed and charged into a high shear mixer. Isopropyl triisostearoyl titanate (0.6 parts, w/w) was blended with liquid paraffin BP (0.6 parts, w/w) to enhance subsequent distribution of the titanate. The titanate mixture was poured or sprayed into the vortex of barium sulphate as the mixer was operated at high speed. Mixing continued for three minutes. The mixture was fed into an extruder with polypropylene chips (40 parts, w/w melt flow index 12) to form suitable pellets. A yarn was then extruded from these pellets in a vertical direction. A drawdown length of greater than 1 m was employed. The melt flow index of the compounded polypropylene would not generally exceed 20.

EXAMPLE 2

Example 1 was repeated with the paraffin oil replaced by toluene (0.6 parts, w/w). Weakening of the filaments by the oil were therefor obviated.

EXAMPLE 3

Example 1 was repeated using barium sulphate (70 parts, w/w, 0.5μ), isopropyl triisostearoyl titanate (0.5 parts, w/w) and powdered polypropylene (29.5 parts w/w,) melt flow index 12. A fibre was spun at a temperature between 190° and 200° C. The resultant fibre had a twist factor of between 4 and 5 turns per inch and a thickness equivalent to 3300 to 3500 decitex. The melt flow index of the compounded polypropylene would not generally exceed 20.

What I claim is:

1. A radio-opaque polypropylene fibre comprising, a coupling agent and 55% to 70% by weight of barium sulphate.

2. A fibre as claimed in claim 1, comprising 60% to 70% of barium sulphate by weight of the fiber.

3. A fibre as claimed in claim 2, comprising 65% to 70% by weight of barium sulphate.

4. A fibre as claimed in claim 1 wherein the coupling agent comprises a titanate.

5. A fibre as claimed in claim 4, wherein the coupling agent comprises an isopropyl trialkanoyl titanate.

6. A fibre as claimed in claim 5, wherein the coupling agent comprises isopropyl triisostearoyl titanate.

7. A fibre as claimed in claim 4, wherein the coupling agent is selected from: isopropyl tridodecylbenzenesulphonyl titanate, isopropyl tri(dioctylphosphate)titanate, isopropyl tri(dioctylpyrophosphate)titanate and titanium di(dioctylpyrophosphate)oxyacetate.

8. A fibre as claimed in claim 1, wherein the polypropylene has a melt flow index not less than 12.

9. A radio-opaque multifilament yarn comprising a plurality of radio-opaque polypropylene fibres, said fibres comprising a coupling agent and 55% to 70% by weight of barium sulphate, wherein said yarn has a predetermined twist factor.

10. A fibre as claimed in claim 9 wherein the twist factor is 1.6 to 2 turns per centimeter.

11. A yarn as claimed in claim 9, wherein the thickness is equivalent to 0.33 to 0.35 gm$^{-1}$.

12. A method of preparation of fibre as claimed in claim 1 wherein powdered barium sulphate combined with the coupling agent is mixed with powdered polypropylene and extruded.

13. A method as claimed in claim 12, wherein the barium sulphate has a particle size of not greater than 0.5μ.

14. A method as claimed in claim 12, wherein the fibre is spun at a temperature of 190°–210° C.

* * * * *